(12) United States Patent
Auberson

(10) Patent No.: US 7,569,337 B2
(45) Date of Patent: Aug. 4, 2009

(54) COUMARINES USEFUL AS BIOMARKERS

(75) Inventor: Yves Auberson, Allschwill (CH)

(73) Assignee: Novartis AG, Basel (CH)

( * ) Notice: Subject to any disclaimer, the term of this patent is extended or adjusted under 35 U.S.C. 154(b) by 640 days.

(21) Appl. No.: 10/506,381

(22) PCT Filed: Mar. 5, 2003

(86) PCT No.: PCT/EP03/02251

§ 371 (c)(1),
(2), (4) Date: Sep. 2, 2004

(87) PCT Pub. No.: WO03/074519

PCT Pub. Date: Sep. 12, 2003

(65) Prior Publication Data

US 2005/0169837 A1    Aug. 4, 2005

(30) Foreign Application Priority Data

Mar. 6, 2002   (GB) .................... 0205281.9

(51) Int. Cl.
*A01N 1/02* (2006.01)
*C07D 401/04* (2006.01)
*C07D 405/05* (2006.01)

(52) U.S. Cl. ............... 435/1.1; 544/362; 544/376

(58) Field of Classification Search ............. 544/362, 544/367, 376; 548/159, 305.1; 435/1.1
See application file for complete search history.

(56) References Cited

U.S. PATENT DOCUMENTS 3,014,041 A * 12/1961 Hausermann et al. ....... 548/159
3,933,847 A * 1/1976 Ohkawa et al. .......... 548/305.1
4,035,740 A * 7/1977 Schafer et al. ............ 372/53

FOREIGN PATENT DOCUMENTS

EP   0 527 433    2/1993
WO   WO 01 77720  10/2001

* cited by examiner

*Primary Examiner*—James O Wilson
*Assistant Examiner*—Ebenezer Sackey
(74) *Attorney, Agent, or Firm*—Foley & Lardner LLP

(57) ABSTRACT

The invention provides compounds of formula (I), wherein R, $R_1$, $R_2$, $R_3$ and $R_4$ are as defined in the description, and their preparation. The compounds of formula I are useful as biomarkers.

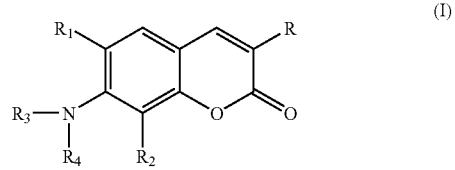

4 Claims, No Drawings

COUMARINES USEFUL AS BIOMARKERS

This application claims the benefit under U.S.C. § 365 (a) of international application No. PCT/EP 03/02251, filed Mar. 5, 2003, which in turn claims the benefit under U.S.C. § 365 (b) and U.S.C. § 119(a) of foreign application GB 0205281.9, filed Mar. 6, 2002.

The present invention relates to novel coumarine derivatives, their preparation, their use as markers and compositions containing them.

More particularly the invention provides a compound of formula I

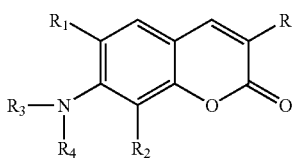

wherein
either $R_1$ and $R_2$ are both hydrogen and either $R_3$ and $R_4$, independently, are H, $CH_3$, $^{11}CH_3$, $(CH_2)_nI$, $(CH_2)_n^{123}I$, $(CH_2)_nOH$, $(CH_2)_nF$ or $(CH_2)_n^{18}F$, n being 2, 3 or 4, or $R_3$ and $R_4$, together with the nitrogen atom to which they are attached, form a group of formula

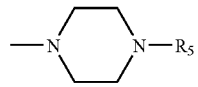

wherein $R_5$ is H, $(CH_2)_nI$, $(CH_2)_n^{123}I$, $(CH_2)_nOH$, $CH_3$, $^{11}CH_3$, $(CH_2)_nF$ or $(CH_2)_n^{18}F$, n being as defined above, or one of $R_1$ and $R_2$ is hydrogen and the other, together with $R_3$, forms a —$(CH_2)_m$—bridge, m being 2 or 3, and $R_4$ is H, $CH_3$, $(CH_2)_nI$, $(CH_2)_n^{123}I$, $(CH_2)_nOH$, $^{11}CH_3$, $(CH_2)_nF$ or $(CH_2)_n^{18}F$, and R is a group of formula

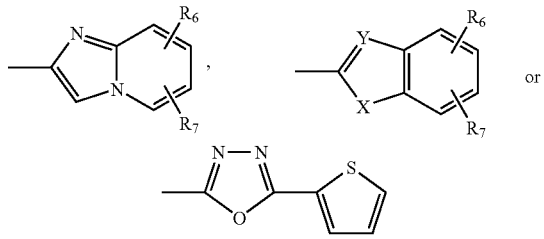

wherein X is O, S or $NR_8$, $R_8$ being H, $CH_3$, $^{11}CH_3$, $(CH_2)_nI$, $(CH_2)_n^{123}I$, $(CH_2)_nOH$, $(CH_2)_nF$ or $(CH_2)_n^{18}F$ (n being as defined above), Y is CH or N and $R_6$ and $R_7$, independently, are H, $NO_2$, F, $^{18}F$, $O(CH_2)_nF$, $O(CH_2)_n^{18}F$, Cl, CN, $^{11}CN$, $OCH_3$, $O^{11}CH_3$, I, $^{123}I$, $O(CH_2)_nI$ or $O(CH_2)_n^{123}I$ (n being as defined above), in free base or acid addition salt form, for use as a marker.

The compounds of formula I, with the exception of the following compounds:
7-Dimethylamino-3-(1-methyl-1H-benzoimidazol-2-yl)-chromen-2-one
3-(1H-Benzoimidazol-2-yl)-7-dimethylamino-chromen-2-one
3-(6-Chloro-benzothiazol-2-yl)-7-dimethylamino-chromen-2-one
3-Benzothiazol-2-yl-7-dimethylamino-chromen-2-one
3-Benzooxazol-2-yl-7-dimethylamino-chromen-2-one
3-Benzooxazol-2-yl-7-methylamino-chromen-2-one
3-(5-Chloro-benzooxazol-2-yl)-7-dimethylamino-chromen-2-one have never been disclosed in the literature and are part of the present invention.

In a further aspect, the invention provides a process for the production of the compounds of formula I and their salts, comprising the steps of a) for the production of a compound of formula I wherein $R_3$, $R_4$, $R_5$, $R_6$, $R_7$ and $R_8$ are different from $^{11}CH_3$, $(CH_2)_n^{18}F$, $(CH_2)_n^{123}I$, $^{18}F$, $O(CH_2)_n^{18}F$, $^{11}CN$, $O^{11}CH_3$, $^{123}I$ and $O(CH_2)_n^{123}I$, reacting a compound of formula II with a compound of formula III

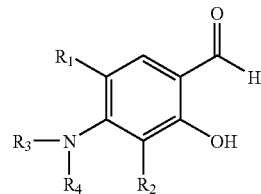

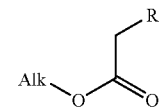

wherein $R_3$ and $R_4$ as well as $R_5$ in $R_3$ and $R_4$; $R_6$ and $R_7$ in R; and $R_8$ in X are different from $^{11}CH_3$, $(CH_2)_n^{18}F$, $(CH_2)_n^{123}I$, $^{18}F$, $O(CH_2)_n^{18}F$, $^{11}CN$, $O^{11}CH_3$, $^{123}I$ and $O(CH_2)_n^{123}I$, and Alk is $(C_{1-4})$alkyl, or b) for the production of a compound of formula I wherein at least one of $R_6$ and $R_7$ is $O^{11}CH_3$, reacting a compound of formula I wherein at least one of $R_8$ and $R_7$ is OH with $I^{11}CH_3$ and a base, or c) for the production of a compound of formula I wherein at least one of $R_6$ and $R_7$ is $O(CH_2)_n^{18}F$, respectively $O(CH_2)_n^{123}I$, reacting a compound of formula I wherein at least one of $R_6$ and $R_7$ is $O(CH_2)_n$OTs or $O(CH_2)_n$OMs with $^{18}F^{\ominus}$, respectively $^{123}I^{\ominus}$, or d) for the production of a compound of formula I wherein at least one of $R_6$ and $R_7$ is $^{18}F$, reacting a compound of formula I wherein at least one of $R_6$ and $R_7$ is $NO_2$ or halogen, with $^{18}F^{\ominus}$, or e) for the production of a compound of formula I wherein at least one of $R_6$ and $R_7$ is $^{123}I$, reacting a compound of formula I wherein at least one of $R_6$ and $R_7$ is $Bu_3Sn$, with $^{123}I$ and hydrogen peroxide, or f) for the production of a compound of formula I wherein at least one of $R_6$ and $R_7$ is $^{11}CN$, reacting a compound of formula I wherein at least one of $R_6$ and $R_7$ is $OSO_2CF_3$ with [$^{11}C$]cyanide, or g) for the production of a compound of formula I wherein at least one of $R_3$, $R_4$, $R_5$ and $R_8$ is $^{11}CH_3$, reacting a compound of formula I wherein at least one of $R_3$, $R_4$, $R_5$ and $R_8$ is hydrogen, with $^{11}CH_3I$, or h) for the production of a compound of formula I wherein at least one of $R_3$, $R_4$, $R_5$ and $R_8$ is $(CH_2)_n{}^{18}F$, respectively $(CH_2)_n{}^{123}I$, reacting a compound of formula I wherein at least one of $R_3$, $R_4$, $R_5$ and $R_8$ is $(CH_2)_n OTs$ or $(CH_2)_n OMs$ with $^{18}F^\ominus$, respectively $I^\ominus$, and recovering the resulting compound of formula I in free base form or in form of an acid addition salt.

The reactions can be effected according to known methods, for example as described in the Examples.

Working up the reaction mixtures and purification of the compounds thus obtained may be carried out in accordance to known procedures.

Acid addition salts may be produced from the free bases in known manner, and vice-versa.

Compounds of formula I In free base or acid addition salt form, hereinafter referred to as agents of the invention, exhibit valuable properties as histopathological staining agents, imaging agents and/or biomarkers, hereinafter "markers".

More particularly the agents of the invention are useful as markers for labeling pathological structures such as intraneuronal neurofibrillary tangles and extracellular β-amyloid plaques, e.g. in the brain of patients with Alzheimer's disease (see Example 5).

The agents of the invention are therefore useful for the early diagnosis and prevention of Alzheimer's disease and for monitoring the effectiveness of therapeutic treatments of Alzheimer's disease.

The advantages of assessing amyloid and neurofibril deposition in vivo and non-invasively using markers capable of labeling these structures have been reported e.g. in WO 00/10614.

In accordance with the above, the present invention provides a composition for labeling histopathological structures in vivo or in vitro, comprising an agent of the invention.

In a further aspect, the present invention provides a method for labeling histopathological structures in vitro or in vivo, which comprises contacting brain tissue with an agent of the invention.

Said brain tissue comprises for example B-amyloid plaques and/or neurofibrillary tangles.

Contacting the brain tissue with the agent of the invention is for example effected by administering the agent of the invention to a patient, e.g. a patient with Alzheimer's disease.

The method of the invention may comprise a further step aimed at determining whether the agent of the invention labeled the target structure.

If the agent of the invention is a non-radioactive compound of formula I, said further step may be effected by observing the target structure using fluorescence microscopy.

If the agent of the invention is a radioactive compound of formula I, said further step may be effected by observing the target structure using positron emission tomography (PET) or single photon emission computed tomography (SPECT).

Labeling histopathological structures in vitro is effected, for example, for detecting histopathological hallmarks of Alzheimer's disease.

Labeling histopathological structures in vivo is effected, for example, for diagnosing Alzheimer's disease in a patient or for monitoring the effectiveness of a therapeutic treatment of Alzheimer's disease.

The following examples illustrate the invention.

EXAMPLE 1

3-Benzothiazol-2-yl-7-[4-(2-fluoro-ethyl)-piperazin-1-yl]-chromen-2-one 200 mg (0.793 mmol) 4-[4-(2-Fluoro-ethyl)-piperazin-1-yl]-2-hydroxy-benzaldehyde and 164 mg (1 eq.) benzothiazol-2-yl-acetic acid methyl ester are heated to reflux for 3 h in 5 mL benzene and 2.5 mL acetonitrile, in the presence of 0.157 mL (2 eq.) piperidine. The reaction mixture is allowed to reach room temperature and the precipitate filtered off, washed with diethylether and dried under high vacuum to yield 90 mg (55%) of desired product as a yellow powder (melting point: 246° C.).

$^1$H-NMR (400 MHz, CDCl$_3$): δ=8.95 (s, 1H); 8.03, 7.97 (2d, 2H); 7.53 (D, 1H); 7.50, 7.39 (2t, 2H); 6.88 (dd,1H); 6.78 (d,1H); 4.62 (dt, 2H); 3.45 (t, 4H); 2.78 (dt, 2H); 2.70 (t, 4H).

The starting materials are prepared as described hereafter:

3-[4-(2-Fluoro-ethyl)-piperazin-1 -yl]-phenol 1 g (5.61 mmol) 3-Piperazin-1-yl-phenol and 0.5 mL (1.25 eq) 1-bromo-2-fluoroethane are stirred 20 h at 60° C. in 5 mL DMF, the reaction mixture allowed to reach room temperature and evaporated, and the residue column chromatographed (silica gel, ethyl acetate/petroleum ether 9:1) to yield 600 mg (48%) of the desired product as a brown oil.

4-[4-(2-Fluoro-ethyl)piperazin-1 -yl]-2-hydroxy-benzaldehyde 600 mg (2.675 mmol) 3-[4-(2-Fluoro-ethyl)-piperazin-1-yl]-phenol are dissolved in 8 mL DMF and cooled to 0° C. 0.27 mL (1.1 eq) POCl$_3$ is added dropwise within 2 min. and the reaction mixture stirred for an additional 5 min. before being allowed to reach room temperature, and then heated and stirred for 3 h at 90° C. The reaction mixture is evaporated and the residue extracted with water and ethyl acetate. The organic phases are washed with brine, dried over sodium sulphate and evaporated. The residue is column chromatographed (silica gel, ethyl acetate followed by ethyl acetate/MeOH 85:15) to yield the desired product as a yellowish oil.

Benzothiazol-2-yl-acetic acid methyl ester 3.2 mL (30 mmol) 2-Amino-thiophenol are dissolved in 100 mL diethylether and treated with 4.17 mL (1 eq.) triethylamine to yield a suspension, to which 3.21 mL (1 eq.) chlorocarbonyl-acetic methyl ester in 10 mL diethylether is added dropwise within 20 min. The resulting suspension is stirred and additional 2 h at room temperature, and the precipitate removed by filtration. The filtrate is evaporated and column chromatographed (silica gel, ethyl acetate/petroleum ether 1:2) to yield the desired product as a yellowish liquid (5.1 g, 82%).

Alternatively, 3-Benzothiazol-2-yl-7-[4-(2-fluoro-ethyl) piperazin-1-yl]-chromen-2-one can be prepared as described hereafter:

10 mg (0.025 mmol) 3-benzothiazol-2-yl-7-[4-(2-hydroxy-ethyl)-piperazin-1-yl]-chromen-2-one are dissolved in 3 mL dichloromethane with 2.5 mg (0.8 eq.) 4-dimethylaminopyridine and 0.013 mL (3 eq.) diisopropylethylamine, and cooled to 0° C. 5.7 mg (1.2 eq.) tosyl chloride are added and the reaction mixture stirred for one hour before being allowed to reach room temperature. After an additional two hours stirring, the reaction mixture is evaporated, the residue taken up in tetrahydrofurane and treated with 0.2 mL tetrabutylammonium fluoride (1M in THF). After stirring for 30 minutes, the solution is evaporated and the desired product obtained as a yellow powder.

MS(EI+): 410 (M+1).

The preparation of the starting material is described in Example 3.

EXAMPLE 2

3-(6-Chloro-imidazo[1,2-a]pyridin-2-yl)-8-(2-fluoro-ethyl)-5,6,7,8-tetrahydro-1-oxa-8-aza-anthracen-2-one 200 mg (0.896 mmol) 1-(2-Fluoro-ethyl)-7-hydroxy-1,2,3,4-tetrahydro-quinoline-6-carbaldehyde and 201 mg (1 eq.) (6-chloro-imidazo[1,2-a]pyridin-2-yl)-acetic acid methyl ester in 6 mL benzene and 3 mL acetonitrile are treated with 0.177 mL (2 eq.) piperidine and refluxed for 18 h. The reaction mixture is allowed to reach room temperature and the precipitate filtered, washed with acetonitrile and dried under high vacuum to yield 240 mg (67%) of desired product as a yellow powder.

$^1$H-NMR (400 MHz, CDCl$_3$): δ=8.59, 8.44, 8.16 (3s, 3H); 7.51, 7.15 (2d, 2H); 7.13 (s, 1H); 4.68, 3.68 (2dt, 2CH$_2$); 3.50, 2.82 (2dt, 2CH$_2$); 1.99 (m, CH$_2$).

MS(EI+): 398 (M+1).

M.p.=290° C. (decomposition).

The starting materials are prepared as described hereafter.

1-(2-Fluoro-ethyl)7-hydroxy-1,2,3,4-tetrahydro-quinoline-6-carbaldehyde 290 mg (1.48 mmol) 1-(2-Fluoro-ethyl)-7-hydroxy-1,2,3,4-tetrahydro-quinolin-7-ol are dissolved in 5 mL DMF. 0.15 mL POCl$_3$ are added dropwise at 0° C. The reaction mixture is slowly heated to 50° C., stirred an additional 3 h at this temperature, then cooled to RT and extracted with ethyl acetate and an aqueous saturated solution of sodium bicarbonate. The combined organic phases are washed with brine, dried over sodium sulphate and evaporated. The residue is column chromatographed (silica gel, ethyl acetate/petroleum ether 1:2) to yield 200 mg (60%) desired product as a brown solid.

1-(2-Fluoro-ethyl)-1,2,3,4-tetrahydro-quinolin-7-ol 500 mg (3.35 mmol) 1,2,3,4-Tetrahydro-quinolin-7-ol are dissolved in 8 mL DMF and stirred at 60° C. overnight with 0.325 mL (1.3 eq) 1-bromo-2-fluoroethane, in the presence of 0.63 mL (1.1 eq) diisopropylethylamine. The reaction mixture is extracted with 0.1 N aqu. HCl and ethyl acetate. The combined organic extracts are washed with brine, dried over sodium acetate and evaporated. The residue is column chromatographed (silica gel, ethyl acetate/petroleum ether 1:2 to 1:1) to yield 290 mg (44%) desired product as a brown oil.

(6-Chloro-imidazo[1,2-a]pyridin-2-yl)-acetic acid methyl ester 1.28 g (10 mmol) 2-Amino-5-chloropyridine and 1.18 mL (1 eq) 4-chloro-3-oxo-butyric acid methyl ester are heated to 115° C. in 15 mL toluene for 18 h. The resulting brown suspension is evaporated and heated 1 h to 90° C. under high vacuum, then cooled to room temperature and stirred in 100 mL dichloromethane, 10 mL saturated aqueous sodium bicarbonate solution and 40 mL water at 0° C. for one hour. The organic phase is then separated and evaporated to yield a brownish solid that is column chromatographed (silica gel, ethyl acetate/petroleum ether 4:1) to yield 700 mg (31 %) desired product as a beige powder. MS(EI+): 225-227 (M+1).

EXAMPLE 3

3-Benzothiazol-2-yl-7-[4-(2-hydroxy-ethyl)-piper-azin-1-yl]-chromen-2-one 240 mg crude 3-benzothiazol-2-yl-7-piperazin-1-yl-chromen-2-one in 10 mL DMF are stirred for 72 h at room temperature in the presence of 858 mg (at least 4 eq.) cesium carbonate and 0.103 mL (at least 2 eq.) 2-iodoethanol. The reaction mixture is extracted with ethyl acetate and a saturated solution of sodium carbonate and washed with brine. The combined organic phases are dried with sodium sulphate and evaporated. The residue is column chromatographed (silica gel, dichloromethane/methanol 95:5+1% conc. NH$_4$OH) to yield 70 mg (26%) desired product as an orange solid.

$^1$H-NMR (400 MHz, CDCl$_3$): δ=8.97 (s, 1H); 8.03, 7.97 (2d, 2H); 7.56 (1d, 1H); 7.50, 7.39 (2t, 2H); 6.89 (d, 1H): 8.78 (s,1H); 3.70 (m, CH$_2$); 3.47, 2.72 (2m, 2×2CH$_2$); 2.64 (m, CH$_2$).

MS(EI+): 408 (M+1).

The starting material is prepared as described hereafter:

3-Benzothiazol-2-yl-7-piperazin-1-yl-chromen-2-one 890 mg (5 mmol) 3-Piperazin-1-yl-phenol are suspended in 100 mL EtOH and treated with 0.42 mL (1 eq.) 12N HCl at a temperature below 10° C. The suspension is stirred an hour and slowly evaporated. The remaining beige powder is dried under high vacuum, then taken up in 60 mL DMF. The solution is cooled to 5° C. under argon, 0.503 mL (1.1 eq.) POCl$_3$ added dropwise and the reaction mixture stirred for an hour at room temperature, then 30 minutes at 80° C., and finally allowed to cool to room temperature, upon which 2 g (3 eq.) solid potassium carbonate is added. The suspension is stirred 30 minutes at room temperature then evaporated, and the residue resuspended and stirred in a 1:1 mixture of dichloromethane and isopropanol. The suspension is filtered, the filtrate evaporated and dried to yield 600 mg crude 2-hydroxy4-piperazin-1-yl-benzaldehyde. This material is taken up in 40 mL of a 1:1 mixture of benzene and acetonitrile, 2.5 mL (5 eq.) piperidine and 683 mg (0.66 eq.) benzothiazol-2-yl-acetic acid methyl ester are added under argon and the reaction mixture refluxed for an hour. The product is extracted with dichloromethane and brine at 0° C., the combined organic phases dried with sodium sulphate, filtered and evaporated, then triturated with diisopropylether to yield 800 mg desired product (crude).

EXAMPLE 4

3-(6-Chloro-imidazo[1,2-a]pyridin-2-yl)-7-[4-(2-fluoro-ethyl)-piperazin-1-yl]-chromen-2-one 253 mg (1 mmol) 4-[4-(2-Fluoro-ethyl)-piperazin-1-yl]-2-hydroxy-benzaldehyde and 450 mg (2 eq.) (6-chloro-imidazo[1,2-a]pyridin-2-yl)-acetic acid methyl ester refluxed in 15 mL benzene and 7.5 mL acetonitrile in the presence of 0.395 mL (4 eq.) piperidine for 21 h. The reaction mixture is cooled to 0° C. and the precipitated material filtered, washed with diethyl ether and dried under high vacuum, yielding 100 mg (23%) desired product as a yellow solid. M.p.=265° C. (decomposition).

EXAMPLE 5

3-Benzothiazol-2-yl-7-(4-methyl-piperazin-1-yl)-chromen-2-one 100 mg (0.28 mmol) 3-Benzothiazol-2-yl-7-piperazin-1-yl-chromen-2-one were dissolved in 15 mL DMF and treated under argon with 183 mg (2 eq.) cesium carbonate, cooled below 5° C. and treated with 1 eq (0.018 mL) MeI. After stirring for 4 h, the reaction mixture is diluted with 100 mL dichloromethane and washed twice with ice-water. The organic phase is evaporated and the residue column chromatographed (silica gel, dichloromethane/EtOH 9:1). Recrystallization from methanol/dichloromethane yields 50 mg (47%) desired product as an orange powder.

MS(EI+): 378 (M+1).

EXAMPLE 6

3-Benzothiazol-2-yl-7-[(2-fluoro-ethyl)-methyl-amino]-chromen-2-one 130 mg (ca. 0.65 mmol) crude 4-[(2-Fluoro-ethyl)-methyl-amino]-2-hydroxy-benzaldehyde and 202 mg (1.5 eq.) benzothiazol-2-yl-acetic acid methyl ester are dissolved in 3 mL acetonitrile and 6 mL benzene, treated with 0.14 mL (2 eq.) piperidine and heated to reflux for 45 minutes. After cooling to room temperature, the crude product is extracted with AcOEt/isopropanol 9:1 and saline, dried over sodium sulfate and evaporated. The crude product is dissolved in 20 mL methanol, and slowly concentrated down to 10 mL at 50° C. The orange crystals are filtered and dried under high vacuum to yield 110 mg (48%) desired product.

M.p.=231-233° C.

The starting materials are prepared as described hereafter:

4-[(2-Fluoro-ethyl)-methyl-amino]-2-hydroxy-benzaldehyde 169 mg (1 mmol) 3-[(2-Fluoro-ethyl)-methyl-amino]-phenol are dissolved in 4 mL DMF and cooled below 10° C. 0.101 mL (1.1 eq.) POCl$_3$ are added dropwise over the course of one minute, the reaction mixture is stirred 10 minutes at room temperature, then heated to 90° C. for 30 minutes. The reaction mixture is allowed to cool to 30° C. and cautiously treated with a slow addition of 8 mL saturated aqueous sodium bicarbonate solution. The desired product is extracted with ethyl acetate and saline, the organic phase dried over sodium sulfate and evaporated to yield 130 mg (66%) crude product as a slightly brownish oil. This compound is used without further purification.

MS(EI+): 198 (M+1).

3-[(2-Fluoro-ethyl)methyl-amino]-phenol 450 mg (2.46 mmol) (2-Fluoro-ethyl)-(3-methoxy-phenylmethyl-amine are dissolved in 1 mL acetic acid and treated with 5 mL of a 33% solution of HBr in acetic acid for 20 h, at 100° C. After cooling to room temperature, the reaction mixture is poured onto ice, treated with 8 mL of a 4N aqueous NaOH solution and extracted with ethyl acetate. The organic phase is washed with saline and an aqueous solution of sodium bicarbonate, then evaporated to yield 400 mg of a brownish oil. The crude product is column chromatographed (silica gel, ethyl acetate/petroleum ether 1:4) to yield 320 mg (77%) of desired product as a brownish resin.

MS(EI+): 170 (M+1).

(2-Fluoro-ethyl)-(3-methoxy-phenyl)-methyl-amine 350 mg (ca. 1 mmol) crude toluene-4-sulfonic acid 2-[(3-methoxy-phenyl)-methyl-amino]-ethyl ester are dissolved in 10 mL THF under argon and treated with 4 mL (4 eq.) of a 1N solution of n-tetrabutylammonium fluoride in THF at 70° C. for 2 h. The reaction mixture is cooled to room temperature and poured onto ice, then extracted with TBME. The organic phase is washed with saline and an aqueous solution of sodium bicarbonate, dried over sodium sulfate and evaporated to yield 180 mg (99%) desired product as a brownish oil. This compound is used without further purification.

MS(EI+): 184 (M+1).

Toluene4-sulfonic acid 2-[(3-methoxy-phenyl)-methyl-amino]-ethyl ester 181 mg (1 mmol) 2-[(3-methoxy-phenyl)-methyl-amino]-ethanol is dissolved in 8 mL dichloromethane and after addition of 0.2 mL (2.5 eq.) pyridine cooled below 5° C. A solution of 489 mg (1.5 eq) p-toluenesulfonic acid anhydride in 4 mL dichloromethane is added dropwise and the reaction mixture stirred at room temperature for 30 minutes before ice and 100 mL TBME are added, followed by 70 mL of a cold aqueous solution of sodium bicarbonate. The organic phase is separated, washed with saline, then dried over sodium sulfate and evaporated. The residue is taken up in toluene and evaporated to yield 350 mg (quant.) crude desired product as a brownish oil. This compound is used without further purification.

$^1$H-NMR (400 MHz, CDCl$_3$): δ=7.70, 7.25 (2d, 2×2H); 7.04 (t, H); 6.24, 6.19 (2d, 2H); 6.11 (br. S, H); 6.89 (d, 1H); 4.17 (t, CH$_2$); 3.78 (s, Me); 3.59 (t, CH$_2$); 2.86, 2.41 (2s, 2Me).

EXAMPLE 7

7-[(2-Fluoro-ethyl)-methyl-amino]-3-(5-thiophene-2-yl-[1,3,4]oxadiazol-2-yl)-chromen-2-one 40 mg (ca. 0.2 mmol) crude 4-[(2-Fluoro-ethyl)-methyl-amino]-2-hydroxy-benzaldehyde and 30 mg (0.13 mmol) (5-thiophen-2-yl-[1,3,4]oxadiazol-2-yl)-acetic acid methyl ester are dissolved under argon in 4 mL benzene and 2 mL acetonitrile, treated with 0.03 mL (2 eq.) piperidine and heated to reflux for 1 h. The reaction mixture is allowed to reach room temperature, evaporated, and the residue column chromatographed (silica gel, AcOEt/petroleum ether 1:1). The fluorescent, yellow product is triturated in diisopropylether, then dried under high vacuum to yield 9 mg (19%) desired product as a yellow powder.

MS(EI+): 372 (M+1).

The starting material (5-thiophen-2-yl-[1,3,4]oxadiazol-2-yl)-acetic acid methyl ester is prepared in a similar manner to the known (5-thiophen-2-yl-[1,3,4]oxadiazol-2-yl)-acetic acid ethyl ester (Heterocycl Commun 2001 7(5):411-416).

EXAMPLE 8

3-(4-Buta-1,3-dienyl-5-methyl-thiazol-2-yl)-7-[4-(3-fluoro-propyl)-piperazin-1yl]-chromen-2-one 50 mg (0.087 mmol) Toluene-4-sulfonic acid 3-[4-(3-benzothiazol-2-yl-2oxo-2H-chromen-7-yl)-piperazin-1-yl]-propyl ester are dissolved in 10 mL anhydrous THF, treated with 0.18 mL of a 1N solution of n-tetrabutylammonium fluoride in THF and heated to 60° C. for 2 h. The reaction mixture is poured onto ice and extracted with dichloromethane after addition of 2 mL aqueous sodium bicarbonate solution. The organic phase is evaporated and the residue column chromatographed (silica gel, dichloromethane/EtOH 98:2) to yield after evaporation and drying under high vacuum 9 mg (26%) desired product as a light brownish powder.

The starting materials are prepared as described hereafter:

Toluene-4-sulfonic acid 3-[4-(3-benzothiazol-2-yl-2-oxo-2H-chromen-7-yl)-piperazin-1-yl]-propyl ester 70 mg (0.16 mmol) 3-Benzothiazol-2-yl-7-[4-(3-hydroxy-propyl)-piperazin-1-yl]-chromen-2-one are dissolved in 15 mL dichloromethane under argon. 0.083 mL Hünig base and 10 mg DMAP are added to the stirred solution, followed by 46 mg (1.5 eq.) tosyl chloride. The reaction mixture is stirred for 20 h at room temperature, poured onto ice, treated with 2 mL aqueous sodium bicarbonate solution and extracted (dichloromethane, saline). The organic phase is evaporated and the residue column chromatographed (silica gel, dichloromethane/EtOH 98:2) to yield after evaporation and drying under high vacuum 73 mg (78%) desired product as a light brownish powder.

MS(EI+): 576 (M+1).

3-Benzothiazol-2-yl-7-[4-(3-hydroxy-propyl)-piperazin-1-yl]-chromen-2-one 320 mg (1 mmol) 3-{4-[3-(tetrahydro-pyran-2-yloxy)-propyl]-piperazin-1-yl}-phenol is dissolved in 10 mL DMF and treated below 10° C. with 0.1 mL POCl$_3$. The reaction mixture is stirred at room temperature for 6 hours, then evaporated and the crude product taken up in 10 mL acetonitrile and treated with 0.6 mL (6 eq.) piperidine. 207 mg benzothiazol-2-yl-acetic acid methyl ester in 10 mL toluene are added and the reaction mixture stirred for 30 minutes at 90° C. before being evaporated. The residue is taken up in 20 mL anhydrous THF, stirred for two hours in the presence of 1 mL of a 6N aqueous HCl solution and evaporated. The residue is taken up in dichloromethane and washed with aqueous sodium bicarbonate and saline. The organic phase is evaporated and the residue column chromatographed (silica gel, dichloromethane/EtOH/aq. NH$_3$ 90:9.9:0.1) to yield 70 mg (17%) desired product as a yellow-orange powder.

MS(EI+): 422 (M+1).

3-{4-[3-(Tetrahydro-pyran-2-yloxy)-propyl]-piperazin-1-yl}-phenol 712 mg (4 mmol) 3-Piperazin-1-yl-phenol are dissolved in 30 mL DMF under argon and cooled below 5° C. After addition of 1.38 g (2.5 eq.) K$_2$CO$_3$, 166 mg (0.25 eq.) KI and 888 mg (1 eq.) 2-(3-bromo-propoxy)-tetrahydro-pyran, the suspension is stirred at room temperature for 20 hours, then extracted with AcOEt after dilution with saline. The organic phase is dried over sodium sulfate, evaporated and the residue column chromatographed (silica gel, AcOEt/EtOH 95:5) to yield 630 mg (48%) desired product as a light yellowish resin.

MS(EI−): 319 (M−1).

EXAMPLE 9

3-Benzooxazol-2-yl-7-(4-methyl-piperazin-1-yl)-chromen-2-one 240 mg (0.79 mmol) 7-(4-Methyl-piperazin-1-yl)-2-oxo-2H-chromene-3-carboxylic acid are dissolved in 12 mL MeOH and heated to 50° C. for three hours in the presence of 2.36 mL KOH in MeOH/water 9:1. After cooling to room temperature, the reaction mixture is acidified with a 6N aqueous HCL solution to pH 2, evaporated and dried under high vacuum to yield a yellow powder. This product is reacted without further purification after dissolution in 10 mL diglyme and 10 mL acetonitrile with 0.115 mL (2 eq.) thionyl chloride and 0.1 mL DMF. The reaction mixture is heated to 70° C. for 90 minutes, cooled to room temperature, concentrated to a volume of 10 mL, and treated with 105 mg (1.2 eq.) 2-Amino-phenol and 400 mg polyphosphoric acid before stirring for 2 h at 170° C. The cooled reaction mixture is extracted with dichloromethane in the presence of an aqueous solution of sodium carbonate, and the organic phase evaporated to yield the amide as a crude product. This compound is dissolved in 10 mL DMF, treated with 0.1 mL POCl$_3$ and heated to 60° C. for three hours. The reaction mixture is cooled to room temperature, treated with an aqueous solution of sodium bicarbonate and extracted with dichloromethane. The organic phase is evaporated and column chromatographed (silica gel, dichloromethane/EtOH/aq. ammonia 90:9.9:0.1). The product is recrystallized from dichloromethane/methanol and dried under high vacuum to yield 20 mg desired product as orange-yellow crystals (7% overall).

MS(EI+): 362 (M+1).

$^1$H-NMR (400 MHz, CDCl$_3$): δ=8.63 (s, 1H), 7.81, 7.59, 7.48, 7.36, 6.84 (5m, 6H); 6.73 (s, 1H); 3.43, 2.58 (2m, 2×2CH$_2$); 2.38 (s, Me).

The starting materials are prepared as described hereafter:

7-(4-Methyl-piperazin-1-yl)-2oxo-2H-chromene-3-carboxylic acid 546 mg (2 mmol) 3-(4-Methyl-piperazin-1-yl)-phenol hydrobromide are dissolved in 15 mL DMF and treated with 0.2 mL (1.1 eq.) POCl$_3$, at a temperature below 5° C. After heating to 50° C. and stirring for 20 hours, the reaction mixture is cooled to room temperature and treated with water. After stirring for an additional two hours, the product is extracted with ethyl acetate in the presence of an aqueous solution of sodium bicarbonate, and the organic phase washed twice with water, dried over sodium sulfate and evaporated to yield 580 mg of a light brown resin which is further used without additional purification.

The intermediate product is dissolved in 10 mL MeOH, treated with 0.23 mL (1 eq.) malonic acid dimethyl ester and 0.02 mL piperidine, refluxed for one hour, cooled to room temperature and evaporated. The residue is column chromatographed (silica gel, dichloromethane/EtOH/aq. ammonia 90:9.9:0.1) to yield 240 mg (39% overall) desired product as a yellow solid.

MS(EI+): 303 (M+1).

EXAMPLE 10

Staining of APP23 Mouse and Human Alzheimer Disease (AD) Brain Sections using an Agent of the Invention or Thioflavine S.

Four-micrometer thick paraffin sections from an APP23 mouse at 26 months of age are deparaffinized in xylene and rehydrated. 10 mg of the compound are dissolved in 1 ml DMSO and diluted with deionized water 1:10. This staining solution is applied on sections for about 20 min. Section background is cleared by washing with 95% ethanol. Finally sections are dehydrated in 99% ethanol, cleared in xylene and mounted with Vectashield™. Sections are investigated using fluorescence microscopy with the following filter combination: Excitation 450-490 nm, emission 510 nm. Twenty micrometer thick dryotom sections from a AD brain cortex are air dried and fixated in 4% PFA for 5 min. After washing in tap water sections are stained either with Thioflavine S or with the compound for 5 min and further processed as described above. The compound is dissolved in DMSO and diluted to a final concentration of 0.01% with 50% Ethanol, Thioflavine S is dissolved in 50% Ethanol, final concentration is 0.01%.

In vivo Labeling of Aβ in APP23 Mice with the Agent of the Invention

Injection solution is prepared fresh by dissolving 10 mg of the compound in 0.2 mL DMSO diluted with 9.8 ml sterile water. Lower concentrations are prepared by further dilution with water. Four APP23 female mice at 21 month of age receive one single injection of the compound (Injection volume: 1 ml/100 gr body weight). The treated animals are killed by decapitation after one hour. The brains are removed and frozen on dry ice. 14 μm thick sections are cut in a cryotome, thawmounted and air-dried. Staining is performed as described above. Sections are analyzed using conventional fluorescence microscopy and confocal microscopy.

Results

1) Staining of APP23 mice brain sections (which contain amyloid deposits but no neurofibrillary tangles):
   The agents of the invention strongly stain amyloid plaques and vascular amyloid deposits in brain sections of APP23 mice.
2) Staining of human AD brain sections (which contain both amyloid deposits and neurofibrillary tangles):
   Brain sections taken from frontal cortex of AD patients are stained with the agents of the invention, and the results compared with a Thioflavine S stain. The agents of the invention intensely and selectively stain amyloid deposits and neurorfibrillary tangles.
3) Ex vivo staining in APP23 mice:
   Intravenous administration of the agents of the invention in APP23 mice leads to a selective and intense staining of amyloid deposits, analyzed ex vivo.

The invention claimed is:

1. A compound of the formula

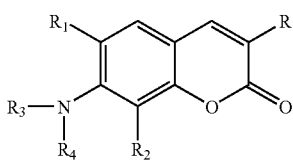

I in which $R_1$ and $R_2$ are both hydrogen;

$R_3$ and $R_4$, together with the nitrogen atom to which they are attached, form a group of the formula

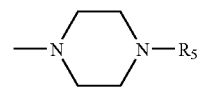

in which $R_5$ is hydrogen, $(CH_2)_nI$, $(CH_2)_n{}^{123}I$, $(CH_2)_n$OH, $CH_3$, $^{11}CH_3$, $(CH_2)_nF$ or $(CH_2)_n{}^{18}F$, n being 2, 3, or 4;

and

R is a group of the formula

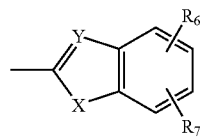

in which X is S, Y is N, and $R_6$ and $R_7$, independently, are hydrogen, $NO_2$, F, $^{18}F$, $O(CH_2)_nF$, $O(CH_2)_n{}^{18}F$, Cl, CN, $^{11}CN$, $OCH_3$, $O^{11}CH_3$, I, $^{123}I$, $O(CH_2)_nI$ or $O(CH_2)_n{}^{123}I$, n being 2, 3, or 4;

in free base form or in acid addition salt form.

2. The compound according to claim 1 of the formula I, which is 3-benzothiazol-2-yl-7-[4-(2-fluoro-ethyl)-piperazin-1-yl]-chromen-2-one, in free base form or in acid addition salt form.

3. A composition for labeling histopathological structures in vitro or in vivo, comprising a compound as defined in claim 1 of the formula I, in free base form or in acid addition salt form.

4. A method for labeling histopathological structures in vitro or in vivo, comprising contacting brain tissue with a compound as defined in claim 1 of the formula I, in free base form or in acid addition salt form.

* * * * *

UNITED STATES PATENT AND TRADEMARK OFFICE
CERTIFICATE OF CORRECTION

PATENT NO. : 7,569,337 B2
APPLICATION NO. : 10/506381
DATED : August 4, 2009
INVENTOR(S) : Yves Auberson It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1248 days.

Signed and Sealed this

Seventh Day of September, 2010

David J. Kappos
*Director of the United States Patent and Trademark Office*